United States Patent
Rohrabacher et al.

[11] Patent Number: 5,207,690
[45] Date of Patent: May 4, 1993

[54] ARRANGEMENT FOR STABILIZING THE HORMONAL EFFECTS PRODUCED BY THE OVARIES OF A SMALL FEMALE MAMMALIAN CREATURE

[75] Inventors: Cliff Rohrabacher, Hampton, N.J.; Scott Mendelson, Champaign, Ill.

[73] Assignee: Bel-Art Products, Inc., Pequannock, N.J.

[21] Appl. No.: 939,148

[22] Filed: Sep. 2, 1992

[51] Int. Cl.⁵ ............................................. A61B 17/00
[52] U.S. Cl. ................................... 606/135; 606/140; 606/141; 128/831; 128/898
[58] Field of Search ............... 606/135, 139, 140, 141, 606/165; 128/831, 843, 898; 279/3

[56] References Cited
U.S. PATENT DOCUMENTS

| | | | |
|---|---|---|---|
| 3,760,810 | 9/1973 | Van Hoorn | 606/140 |
| 3,856,018 | 12/1974 | Perisse | 606/139 |
| 3,911,923 | 10/1975 | Yoon | 606/141 |
| 3,989,049 | 11/1976 | Yoon | 128/831 |
| 4,038,988 | 8/1977 | Perisse | 606/139 |
| 4,257,419 | 3/1981 | Göltner | 606/140 |
| 5,100,419 | 3/1992 | Ehlers | 606/140 |

Primary Examiner—Stephen C. Pellegrino
Assistant Examiner—Jeffrey A. Schmidt
Attorney, Agent, or Firm—Anthony F. Cuoco

[57] ABSTRACT

An arrangement including a suction pump, a pipette, an application tip and a plurality of ligating rings which are carried on the application tip. The application tip is disposed in cooperative relation with the pipette so that the ligating rings may be transferred from the adapter tip to the pipette while being gradually stretched. The pipette is disposed in an incision exposing the ovarian sack of a small mammalian creature, whereupon a suction or vacuum is generated by the pump to capture the ovarian sack, after which a ligating ring is slipped off of the pipette and contracts to ligate said captured sack. This enables resorption of the ligated ovarian sack into the creature and stabilization of hormonal activity as is desired for experimental purposes.

4 Claims, 2 Drawing Sheets

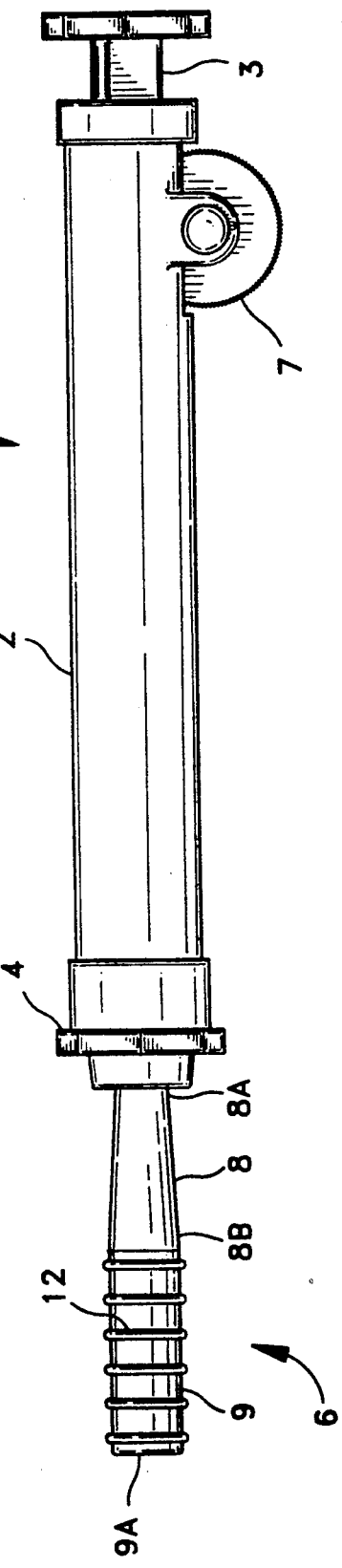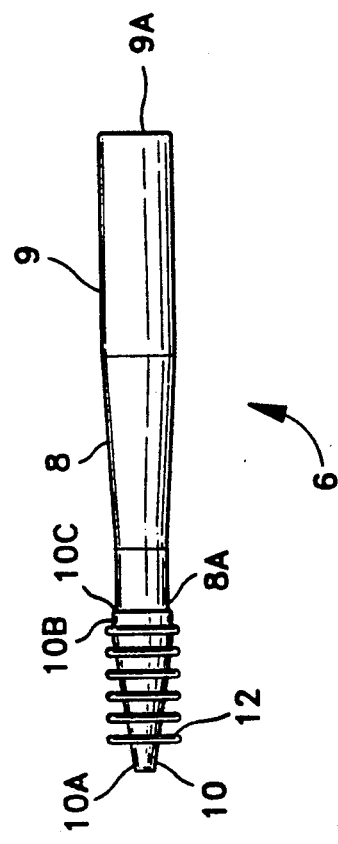

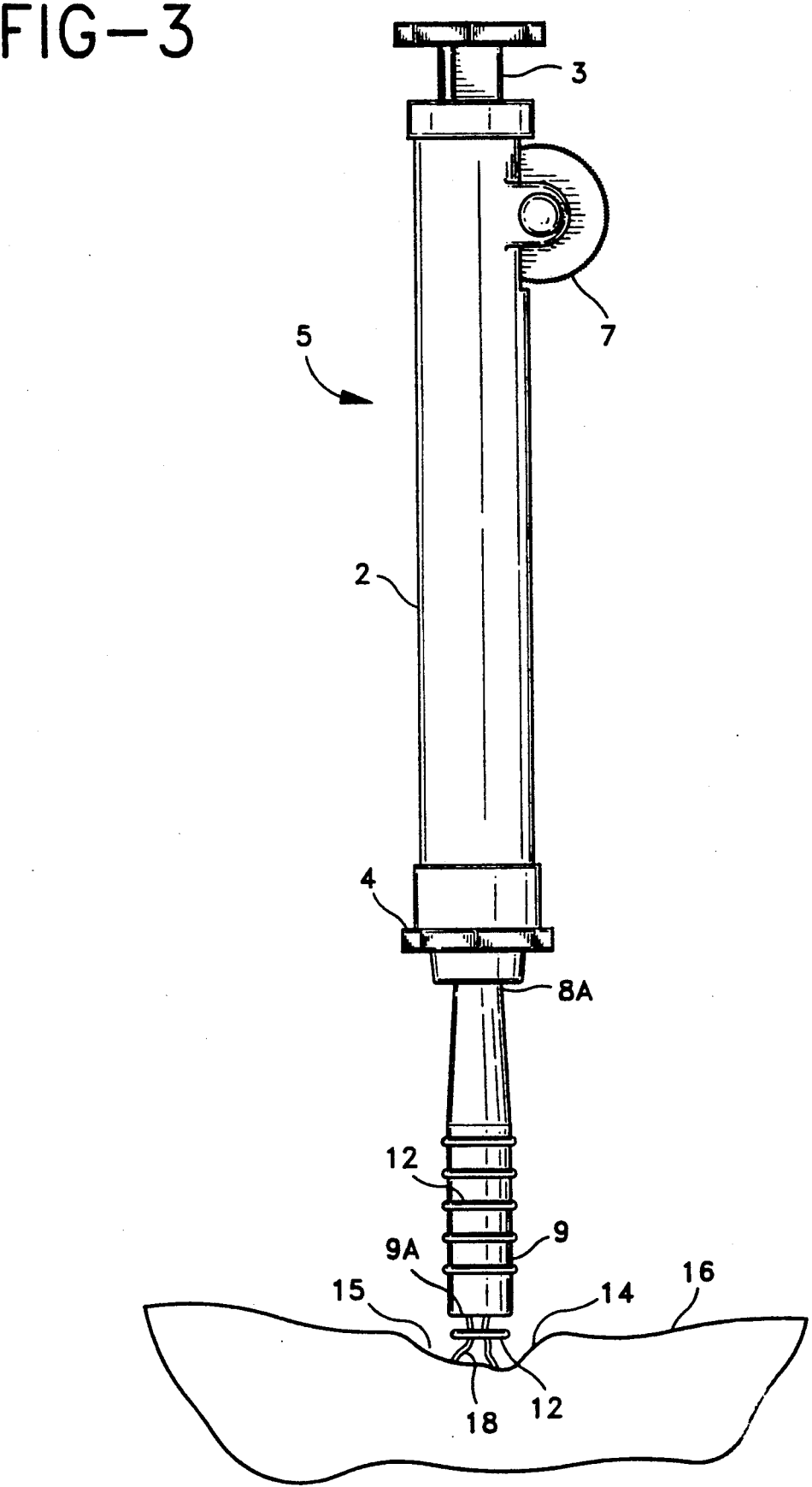

ARRANGEMENT FOR STABILIZING THE HORMONAL EFFECTS PRODUCED BY THE OVARIES OF A SMALL FEMALE MAMMALIAN CREATURE

BACKGROUND OF THE INVENTION

Small female mammalian creatures, such as rats or the like, are used in various laboratory experiments, wherein the hormonal effects produced by the ovaries of the creatures interfere with the results of the experiments. This is particularly true when the experiments involve procedures dealing with neuroreceptor effects. It should be noted that small female mammalian creatures tend to be better subjects for this experimental work but the hormones released by their ovaries naturally cause unaccountable alterations in many of their bodily systems and subsystems. Accordingly, in order to achieve valid experimental results, these hormonal effects must be stabilized. This is accomplished by rendering the ovaries of the mammalian creature inactive so as to stabilize the hormonal effects produced thereby.

Prior to the present invention, accomplishing the above involved incising the uterine horn of the creature or manually ligating the end of same. Both involve delicate and time consuming procedures.

The present invention accomplishes the desired result in a more simple and direct manner. After an incision is made in the usual manner to expose the uterine cavity, a vacuum arrangement is used to extract the ovarian sack from the cavity. The extracted sack is then ligated with a ligating member. The resultant effect is to isolate the ovarian sack from the normal functions of the mammalian creature. The ligated ovarian sack is resorped into the exposed cavity and hormonal activity as would otherwise occur stabilizes, as is desireable for the aforementioned purposes.

The applicants herein are aware of several patented devices which teach extracting a bodily member via vacuum means and then ligating the member for one reason or another. The following patents are noted in this regard.

U.S. Pat. No. 5,100,419 (U.S. Class 606-140) which issued on Mar. 31, 1992 to Ehlers relates to removing diverticula in the colon. The apparatus disclosed includes a reciprocating vacuum tube for inverting the diverticulum and a caliper for placing a fastening device, such as an elastic band, around the base of the inverted diverticulum. The means for stretching and slipping the rubber band over the diverticula and releasing said rubber band to tightly engage said diverticula at said base involves a rather complicated arrangement and differs structurally than that of the invention herein disclosed.

U.S. Pat. No. 5,083,556 (U.S. Class 128/79) which issued to Osbon, et al on Jan. 28, 1972 relates to a penile cincture structure. The subject's male organ is placed within a vacuum chamber or cylinder for producing engorgement, and which condition may be subsequently secured with an elastic cincture band or the like. Here again, the structural arrangement involved differs from that of the invention herein disclosed.

U.S. Pat. No. 4,257,419 which issued to Goltner, et al on Mar. 24, 1981 relates to a suction assisted hemorrhoid ligator. The patent teaches using vacuum to extract a tissue member and then pinching off the extracted member with an elastic band or the like. Likewise, this patent teaches an entirely different structure than that of the invention herein disclosed.

U.S. Pat. No. 823,877 which issued to Kellogg on Jun. 19, 1906 is of interest to the extent that it relates to applying a compressant rubber ring to the stump of an umbilical cord of a newborn infant after cutting off same so as to prevent hemorrhage. Unlike the present invention, the device of the patent does not involve the use of vacuum.

SUMMARY OF THE INVENTION

This invention contemplates an arrangement for stabilizing the hormonal effects produced by the ovaries of a small female mammalian creature, including a plurality of elastic ligating rings, a suction or vacuum pump, a tapered pipette and a tapred application tip. The application tip is arranged to carry a plurality of elastic ligating rings and receives an end of the pipette when in use. The arrangement is such that the plurality of rings can be transferred from the adapter tip to the pipette while being gradually stretched. The pipette is inserted into the vacuum pump. After an incision is made in a subject mammalian creature in the area of the ovarian sack, the ovarian sack is captured by disposing the pipette adjacent the sack and actuating the pump. When the user determines that the ovarian sack is fully captured and exposed, a ligating ring is maneuvered from the pipette over the ovarian sack at its base to ligate the sack. The pump is actuated to release the ligated sack and the incision previously made is closed in a manner best determined by the user. The resultant effect is to isolate the ovarian sack from the normal functions of the mammalian creature. This enables a resorption of the sack as well as a stabilization of hormonal activity, as would otherwise not occur.

BRIEF DESCRIPTION OF THE DRAWINGS

FIG. 1 is a diagrammatic representation illustrating components of the invention.

FIG. 2 is a diagrammatic representation particularly illustrating an application tip having ligating rings carried thereon and arranged with a pipette so that the rings can be transferred thereto.

FIG. 3 is a diagrammatic representation illustrating the use of the invention.

DETAILED DESCRIPTION OF THE INVENTION

With reference to FIG. 1, a pump is designated by the numeral 2. A chuck 4 is supported by pump 2 and which chuck, in turn, supports a pipette 6.

Pipette 6 is a tubular member having a section 8 which tapers from an end 8A which is received by chuck 4 to an end 8B having a diameter larger than that of end 8A, and thereafter has a straight section 9 which terminates at an end 9A.

An adapter tip shown in FIG. 2 is designated by the numeral 10 and tapers from a diameter 10A to a larger diameter 10B having an internal recess 10C. Recess 10C of adapter tip 10 is sized to receive diameter 8A of pipette section 8.

Adapter tip 10 as shown in FIG. 2 carries a plurality of elastic ligating rings 12 which are shown for illustration purposes as six in number. The ligating rings are slipped over end 10A of adapter tip 10 toward end 10B thereof.

With reference to FIGS. 1 and 2, ligating rings 12 are transferred from adapter tip 10 to pipette 6. This is accomplished when recess 10C of adapter tip 10 receives end 8A of pipette section 8. The ligating rings are gently pushed off of the adapter tip by a user on to tapered pipette section 8 and therefrom on to straight pipette section 9, whereby the device of the invention is ready for use. When the transfer of the ligating rings has been completed, adapter tip 10 is removed to a remote location and additional ligating rings may be disposed thereon in readiness for another transfer of ligating rings to the pipette, as will now be understood. It will be readily appreciated that with the arrangement described, ligating rings 12 are gradually stretched as best serves the purposes of the invention. Pipette 6 is supported at end 8A by pump 2 via chuck 4 which reserves said end 8A.

Pump 2 is of a conventional type having a reciprocating piston 3 operated so as to move in and out of a cylinder 5 via a notched thumb wheel 7 in either the clockwise or counterclockwise directions via a gear and pinion arrangement. When thumb wheel 7 is actuated in one direction, a vacuum or suction is created and when actuated in the opposite direction, the vacuum or suction is released. Pump 2 will be recognized as being of a conventional type, such as manufactured and marketed under the trade designation THE PIPETTE PUMP by BelArt Products, Inc., Pequannock, New Jersey, and illustrated at page 104 of their catalog 283.

With reference to FIG. 3, an incision 14 is made in a small mammalian creature, such as a rat, designated by the numeral 16 to expose the creature's uterine cavity 15. End 9A of pipette section 9 is disposed adjacent ovarian sack 18 of creature 16, and which ovarian sack is visible and recognizable by a user through incision 14. The ovarian sack is captured by actuating thumb wheel 7 of pump 2 to create a vacuum or suction which draws ovarian sack 18 out of uterine cavity 15. When the user determines that the ovarian sack is fully captured, a ligating ring 12 is maneuvered off of pipette section 9 over ovarian sack 18 at its base. The arrangement is such that elastic ligating ring 12, which has been gradually stretched to fit over pipette section 9 as aforenoted now contracts to ligate the ovarian sack. With the ovarian sack thus ligated, pump 2 is actuated via thumb wheel 7 to release the vacuum or suction on ligated sack 18, whereupon the ligated sack is urged by the user into cavity 15. Incision 14 is then closed as best determined by the user.

The effect of the aforegoing is to isolate the ovarian sack from the bodily functions of creature 16. The ovarian sack is resorped into the creature and all hormonal effects as would otherwise be generated by active ovaries are stabilized, whereby the creature is rendered more adaptable to experiments or the like as is desireable.

In this regard, it will be understood that ligation rings 12 are of a twenty-five to thirty durometer elastic silicone, rubber or latex material. Rings of this type may be gradually stretched to several times their original inside diameter and after being held at tension for an undetermined time, as on pipette section 9, are able to snap back to their original inside diameter to satisfy the purposes of the invention.

Pump 2 may be entirely of plastic and pipette 6 may be of glass or plastic, as is adapter tip 10, so as to facilitate cleaning of the components of the invention as may be necessary from time to time.

In practice, the ligating rings may be slipped off of pipette section 9 with a small pair of forceps. Lubrication with glycerine will allow the ligating rings to be removed from the pipette section quite easily.

There has thus been described apparatus simple in construction and easy to use for ligating the ovaries of a small mammalian creature whereby the creature is rendered more adaptable for experimental purposes or the like. The device eliminates complicated procedures which have otherwise been required and reduces the time necessary to stabilize the creature's ovarian activity. This is an important consideration in laboratory procedures wherein a multiplicity of creatures need to be treated within a relatively short period of time as experimental protocols may require.

With the above description of the invention in mind, reference is made to the claims appended hereto for a definition of the scope of the invention.

What is claimed is:

1. Arrangement for stabilizing the hormonal effects produced by the ovaries of a small female mammalian creature, comprising:
   a ligating ring application member;
   a plurality of elastic ligating rings disposed on the ligating ring application member;
   a pipette member having first and second ends;
   the ligating ring application member having a recess for removably receiving the first end of the pipette member, whereupon the plurality of elastic ligating rings can be user-transferred from the ligating ring application member to the pipette member;
   vacuum pump means including a chuck member for coupling the pipette member at the first end thereof to the vacuum pump means;
   the second end of the pipette member disposed adjacent an exposed ovarian sack in the uterine cavity of a small female mammalian creature;
   the vacuum pump means being user-actuated to create a vacuum through the pipette member for capturing the ovarian sack and for drawing said sack out of the uterine cavity, whereupon a ligating ring is user-maneuvered off of the pipette member and over the ovarian sack to ligate said sack at its base; and
   the vacuum pump means being user-actuated to release the vacuum on the ligated ovarian sack, whereupon said sack is user-urged into the uterine cavity for being resorped into the creature so that the creature's hormonal effects are stabilized.

2. An arrangement as described by claim 1, wherein:
   the ligating ring application member tapers from one diameter at one end to an other larger diameter at the opposite end; and
   the recess for removably receiving the first end of the pipette member being in the opposite end.

3. An arrangement as described by claim 2, wherein the pipette member is a tubular member having a section which tapers from one diameter at the first end of the pipette member to an other larger diameter, and having a straight section extending from the other larger diameter and terminating at the second pipette member end.

4. A method for stabilizing the hormonal effects produced by the ovaries of a small mammalian creature, comprising;
   disposing a plurality of elastic ligating rings on an increasingly tapered ligating ring application member;
   transferring the plurality of ligating rings from the application member to a pipette member including transferring the ligating rings from the increasingly tapered application member to an increasingly tapered section of the pipette member and therefrom to a straight section of said pipette member for gradually stretching the rings, with said rings contracting to ligate the ovarian sack when maneuvered off of said straight section of the pipette member;

coupling the pipette member to a vacuum pump;

disposing the pipette member adjacent an exposed ovarian sack in the uterine cavity of a small mammalian creature;

actuating the pump to create a vacuum through the pipette for capturing the exposed ovarian sack and for drawing said sack out of the uterine cavity;

maneuvering a ligating ring off of the pipette member and over the ovarian sack to ligate said sack;

actuating the pump to release the vacuum on the ligated sack; and urging the sack into the uterine cavity so that the sack is resorped by the creature for stabilizing the creature's hormonal effects.

* * * * *